United States Patent [19]
Black et al.

[11] Patent Number: 5,436,265
[45] Date of Patent: Jul. 25, 1995

[54] 1-AROYL-3-INDOLYL ALKANOIC ACIDS AND DERIVATIVES THEREOF USEFUL AS ANTI-INFLAMMATORY AGENTS

[75] Inventors: Cameron Black, Pointe Claire; Joseph A. Mancini, St. Leonard; Cheuk K. Lau, Ile Bizard; Petpiboon Prasit, Kirkland; Philip J. Vickers, Pierrefonds, all of Canada

[73] Assignee: Merck Frosst Canada, Inc., Kirkland, Canada

[21] Appl. No.: 152,620

[22] Filed: Nov. 12, 1993
(Under 37 CFR 1.47)

[51] Int. Cl.⁶ .............. A61K 31/40; A61K 31/405; C07D 209/12
[52] U.S. Cl. .................. 514/420; 514/419; 548/500
[58] Field of Search ............... 514/420, 419; 548/500

[56] References Cited

U.S. PATENT DOCUMENTS

| | | | |
|---|---|---|---|
| 3,161,654 | 12/1964 | Shen et al. | 548/500 |
| 3,647,858 | 3/1972 | Hinkley et al. | 560/11 |
| 3,654,349 | 4/1972 | Shen et al. | 562/428 |
| 4,868,201 | 9/1989 | Fukaya et al. | 514/420 |

OTHER PUBLICATIONS

Chemical Abstracts vol. 106:50037v, 1987, Fukaya et al, "Indoleacetic Acid Derivatives."
Chemical Abstracts vol. 91:102002y, 1979, Stochla et al, "Antiinflammatory activity of . . . in immunological and non-immunological tests".
Chemical Abstracts vol. 64, 1966, Abstract 6622b, "α-1 (Aroyl-3-indolyl)acetic Acids".
Chemical Abstracts vol. 59, 1963, abstract 8707e, "Indoles."
Chemical Abstracts, vol. 62, 1965, abstract 16198e, "Indole acid Amides."
Advances in Drug Research, vol. 12, 1977 p. 145, Harper, N. J. et al, New York.
Agnew. Chem. Internat. Edit. vol. 11 (1972) No. 6 pp. 460–472, "Perspectives in Nonsteroidal Anti–Inflammatory Agents", T. Y. Shen.
Arzneim.Forsch. Drug Res. 30 (II), Nr. 8a (1980) Boltze, et al. pp. 1314–1325.

*Primary Examiner*—Jacqueline Haley
*Attorney, Agent, or Firm*—Curtis C. Panzer; David L. Rose

[57] ABSTRACT

Compounds of the structures shown below are specific inhibitors of cyclooxygenase-2 useful in the treatment of cyclooxygenase-2 mediated disease states such as inflammation, pain and fever, and are non-ulcerogenic.

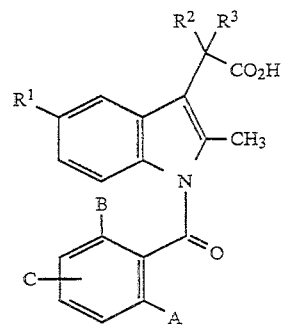

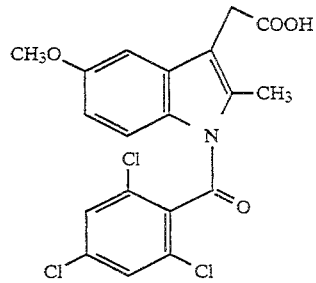

8 Claims, No Drawings

1-AROYL-3-INDOLYL ALKANOIC ACIDS AND DERIVATIVES THEREOF USEFUL AS ANTI-INFLAMMATORY AGENTS

BACKGROUND OF THE INVENTION

This invention relates to novel N-acylindoles and related compounds; to methods of treating cyclooxygenase mediated diseases with the novel compounds; and to certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1)or the constitutive enzyme, as originally identified in bovine seminal vesicles. More recently the gene for a second inducible form of cyclooxygenase (cyclooxygenase-2) (COX-2) has been cloned, sequenced and characterized initially from chicken, murine and human sources. This enzyme is distinct from the cyclooxygenase-1 which has been cloned, sequenced and characterized from various sources including the sheep, the mouse and man. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions, have potential anti-cancer effects and be useful in the treatment of Alzheimer's disease, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

U.S. Pat. Nos. 3,161,654, 3,647,858 and 3,654,349 disclose compounds similar to those of the present invention. It has now been unexpectedly found that compounds with a substituent A in structure I fixed in the ortho position of the phenyl group attached to Y exhibit marked selectivity for the inhibition of Cox-2 over Cox-1.

SUMMARY OF THE INVENTION

This invention relates to the novel compound of Formula I.

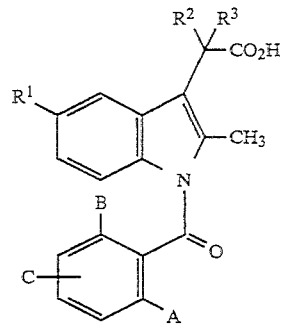

The invention also relates to certain pharmaceutical compositions for treatment of cyclooxygenase-2 mediated diseases comprising compounds of Formula I; to a method of treating cyclooxygenase-2 mediated diseases comprising administration to a patient in need of such treatment of a non-toxic therapeutically effective amount of a compound of Formula I; and to process for the preparation of the novel compounds of Formula I.

DETAILED DESCRIPTION OF THE INVENTION

The novel compound of this invention is represented by structural Formula I:

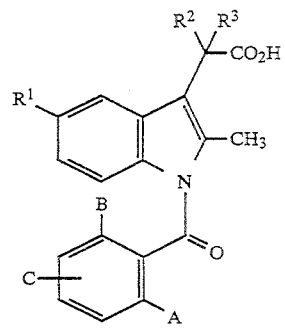

or a pharmaceutically acceptable salt thereof, wherein:
$R^1$ is $-OCH_3$, $-N(CH_3)_2$, $-SCH_3$, $OCF_3$, halo, or lower alkyl;
$R^2$ and $R^3$ are independently H or lower alkyl or $R^2$ and $R^3$ may be joined to form a saturated hydrocarbon ring of 3 to 7 members;
A is halogen, lower alkyl, lower alkoxy, lower alkylthio, lower alkylsulfinyl, lower alkylsulfonyl, $CF_3$, CN, $N_3$, $NO_2$, $SCF_3$ or $OCF_3$;
B is A or also H if A is $CF_3$;
C is A or H with the proviso that if A is $CF_3$, B and C are not both H;

For purposes of the present specification the following terms have the indicated meanings.

"Lower alkyl" means alkyl groups of from 1 to 7 carbon atoms of a straight, branched or cyclic configuration. Examples of lower alkyl groups include methyl, ethyl, propyl, isopropyl, butyl, s- and t-butyl, pentyl, hexyl, heptyl, cyclopropyl, cyclobutylmethyl, cycloheptyl, and the like.

"Lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Lower alkylthio" means alkylthio groups of from 1 to 7 carbon atoms of a straight, branched or cyclic configuration. Examples of lower alkylthio groups include methylthio, propylthio, isopropylthio, cycloheptylthio, and the like. By way of illustration, the propylthio group signifies —$SCH_2CH_2CH_3$.

"Lower alkylsulfinyl" means those alkylsulfinyl groups of from 1 to 7 carbon atoms of straight, branched or cyclic configuration. Examples of lower alkylsulfinyl grups are methylsulfinyl, 2-butylsulfinyl, cyclohexylmethylsulfinyl, and the like. By way of illustration the 2-butylsulfinyl group signifies —$S(O)CH(CH_3)CH_2CH_3$.

"Lower alkylsulfonyl" means those alkylsulfonyl groups of from 1 to 7 carbon atoms of a straight, branched or cyclic configuration. Examples of lower alkylsulfonyl groups are methylsulfonyl, 2-butylsulfonyl, cyclohexylmethylsulfonyl, and the like. By way of illustration the 2-butylsulfonyl group signifies —$S(O)_2CH(CH_3)CH_2CH_3$.

Halogen includes F, Cl, Br, and I.

Some of the compounds described herein contain one or more asymmetric centers and may thus give rise to diastereomers and optical isomers. The present invention is meant to comprehend such possible diastereomers and mixtures thereof as well as their racemic and resolved, enantiomerically pure forms and other mixtures of the enantiomers and pharmaceutically acceptable salts thereof.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betnine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

One embodiment of the novel compounds of this invention is that with structural formula:

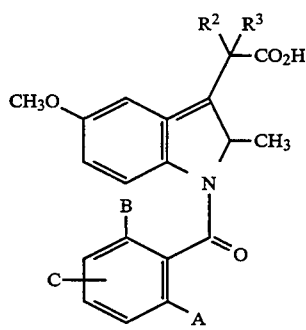

Specific compounds representative of this embodiment are those depicted in Table I.

TABLE I

| A | B | C | $R^2$ | $R^3$ |
|---|---|---|---|---|
| Cl | Cl | 4-Cl | H | H |
| Cl | Cl | 4-Cl | $CH_3$ | H |
| Cl | Cl | H | H | H |
| $CF_3$ | H | 4-$CF_3$ | H | H |
| $CF_3$ | $CF_3$ | H | H | H |
| F | F | H | H | H |
| Cl | F | H | H | H |
| Br | Cl | H | $CH_3$ | H |
| Br | Cl | 4-Cl | H | H |
| $CF_3$ | Cl | 4-Cl | $CH_3$ | $CH_3$ |
| $OCH_3$ | $OCH_3$ | H | H | H |
| Cl | Cl | 4-$S(O)_2CH_3$ | H | H |
| Cl | Cl | 4-$SCH_3$ | H | H |
| Cl | Cl | 4-$S(O)CH_3$ | H | H |
| $CH_3$ | $CH_3$ | H | H | H |
| $CH_3$ | Cl | 4-Cl | H | H |
| $NO_2$ | Cl | H | H | H |
| $SCH_3$ | Cl | 4-Cl | H | H |
| CN | Cl | H | H | H |
| I | Cl | H | H | H |
| $N_3$ | Cl | H | H | H |
| $SCF_3$ | Cl | 4-Cl | H | H |
| $OCF_3$ | Cl | H | H | H |
| $S(O)_2CH_3$ | Cl | 4-Br | H | H |

Another embodiment of the novel compounds of the present invention is the compound of the following structure:

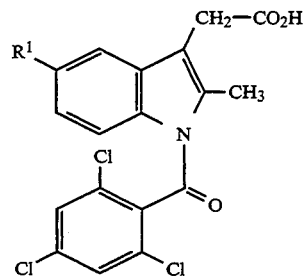

Specific compounds representative of this structure are indicated in Table II.

TABLE II

| $R^1$ |
|---|
| F |
| Cl |
| $CH(CH_3)_2$ |
| $N(CH_3)_2$ |
| $S—CH_3$ |
| $OCF_3$ |

It will be understood that in the discussions of pharmaceutical compositions and methods of treatment which follow, references to the compounds of Formula I are meant to also include the pharmaceutically acceptable salts.

Another embodiment of this invention comprises the method of treatment using the Compound of Formula I for the relief of pain, fever and inflammation of a variety of conditions including rheumatic fever, symptoms associated with low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, and following surgical and dental procedures. Compound 1 may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labor and asthma.

By virtue of its high cyclooxygenase-2 (COX-2) activity and/or its specificity for cyclooxygenase-2 over cyclooxygenase-1 (COX-1), compound I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

A fourth embodiment of this invention includes pharmaceutical compositions comprising the compound of Formula I as active ingredient. For the treatment of any of these cyclooxygenase mediated diseases compound I may be administered orally, topically, parenterally, by inhalation spray or rectally in dosage unit formulations containing conventional non-toxic pharmaceutically acceptable carders, adjuvants and vehicles. The term parenteral as used herein includes subcutaneous injections, intravenous, intramuscular, intrastemal injection or infusion techniques. In addition to the treatment of warm-blooded animals such as mice, rats, horses, cattle sheep, dogs, cats, etc., the compound of the invention is effective in the treatment of humans.

In further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I, optionally co-administered with one or more of such ingredients as listed immediately above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the an for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. For purposes of this application, topical application shall include mouth washes and gargles.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carder material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

In the process discussions and the Examples that follow, the following abbreviations have the indicated meanings:

| | |
|---|---|
| DMAP = | 4-(dimethylamino)pyridine |
| HMPA = | hexamethyl phosphoric triamide |
| KHMDS = | potassium hexamethyldisilazane |
| NSAID = | non-steroidal anti-inflammatory drug |
| r.t. = | room temperature |
| rac. = | racemic |
| THF = | tetrahydrofuran |
| TLC = | thin layer chromatography |
| $C_3H_5$ = | allyl |
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

The compounds of the present invention can be prepared according to the following methods.

Method A

The indolyl compounds (IV) are easily prepared from the condensation of substituted phenylhydrazines II with substituted levulinic ethyl esters III, as described in a U.S. Pat. No. 3,161,654. After hydrolysis of the ester and esterification with 2-trimethylsilylethanol in the presence of 1-(3-Dimethylaminopropyl)-3-ethyl-carbodiimide•HCl and DMAP, the ester derivatives V are obtained. The acylation of the nitrogen can be achieved by deprotonation of the nitrogen with KHMDS in THF/HMPA followed by the addition of an appropriate benzoyl chloride VI to afford VII. The 2-(trimethylsilyl)ethyl ester group can be then removed by fluoride treatment (TBAF).

Method B

The formation of a saturated ring (X) may be accomplished from VII when $R^2=R^3=H$ by deprotonation and bis-alkylation with a dihalogenated alkyl (Dox et al., J. Am. Chem. Soc. 1921, p. 2097 and Stewart et al., J. Org. Chem. 1965, p. 1451.

Method A

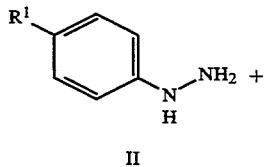

II

-continued
Method A

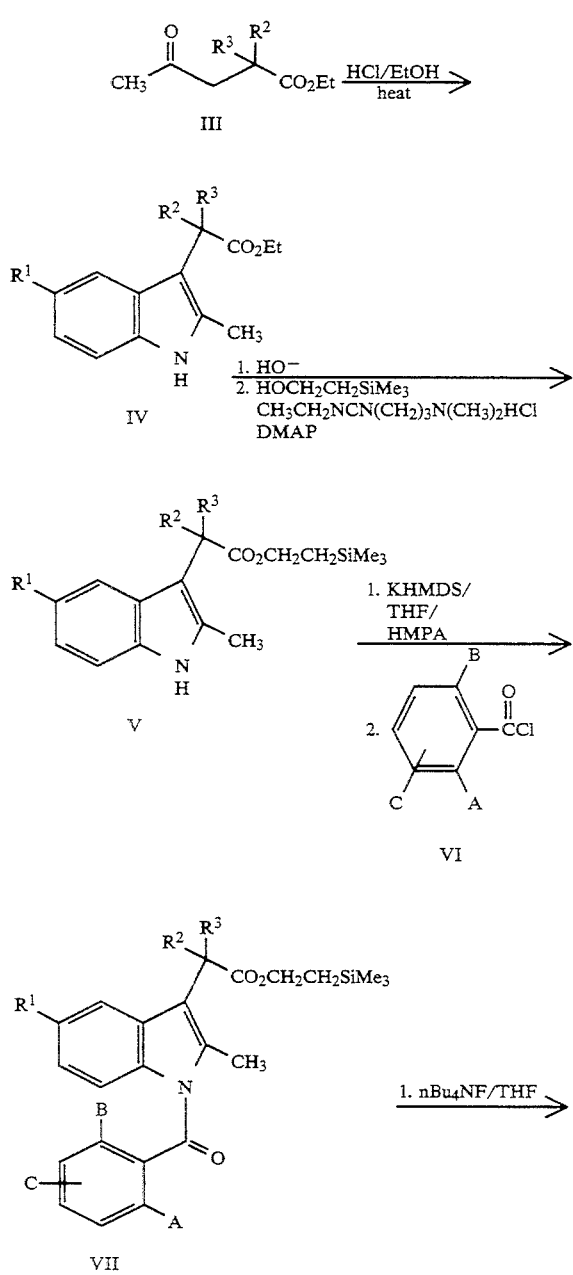

Method B

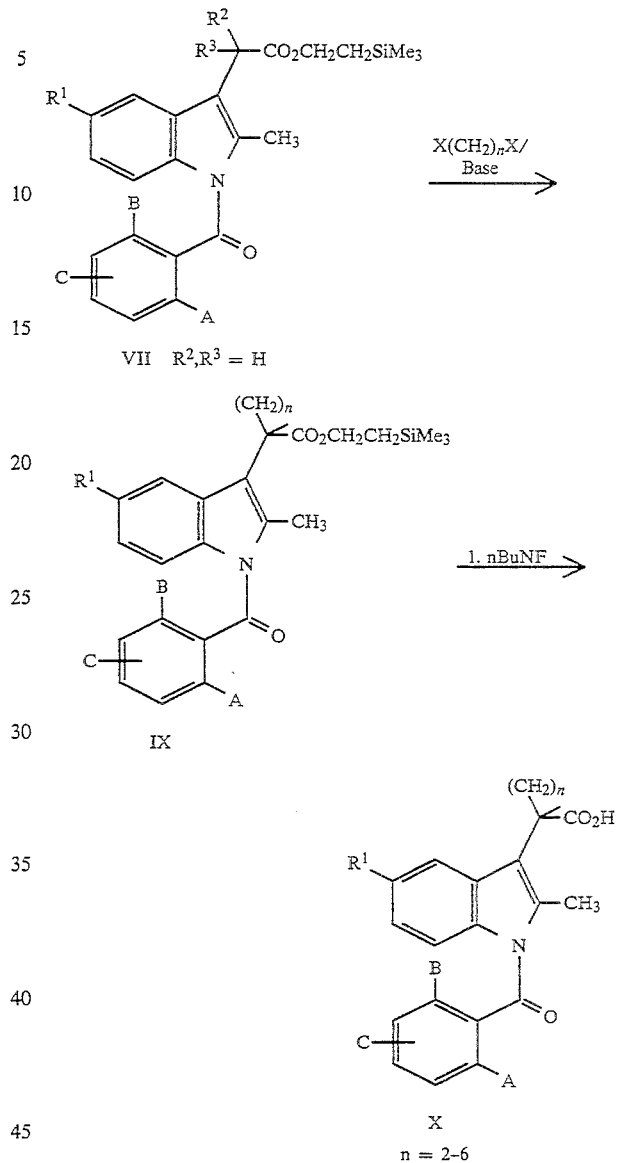

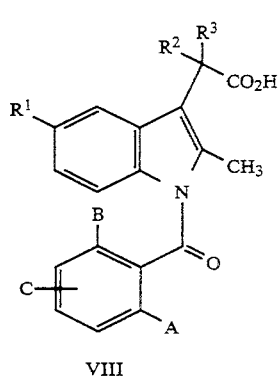

The compound of Formula I can be tested using the following assays to determine their cyclooxygenase-2 inhibiting activity.

Inhibition of Cyclooxygenase Activity

Compounds were tested as inhibitors of cyclooxygenase activity in whole cell and microsomal cyclooxygenase assays. Both of these assays measured prostaglandin $E_2$ synthesis in response to arachidonic acid, using a radioimmunoassay. Cells used for whole cell assays, and from which microsomes were prepared for microsomal assays, were human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence of arachidonate addition.

Rat Paw Edema Assay—Protocol

Male Sprague-Dawley rats (150–200 g) were fasted overnight and were given po either vehicle (1% methocel) or a test compound. One hr later, a line was drawn using a permanent marker at the level above the ankle in one hind paw to define the area of the paw to be monitored. The paw volume ($V_o$) was measured using a plethysmometer (Ugo-Basile, Italy) based on the principle of water displacement. The animals were then injected subplantarly with 50 µl of 1% carrageenan solution in saline (FMC Corp, Maine) into the paw using an insulin syringe with a 25-gauge needle (i.e. 500 µg carrageenan per paw). Three hr later, the paw volume ($V_3$) was measured and the increases in paw volume ($V_3-V_0$) were calculated. The animals were sacrificed by $CO_2$ aphyxiation and the absence or presence of stomach lesions scored. Data were compared with the vehicle-control values and percent inhibition calculated. Since a maximum of 60–70% inhibition (paw edema) was obtained with standard NSAIDs, $ED_{30}$ values were used for comparison. All treatment groups were coded to eliminate observer bias.

Compounds of the present invention are inhibitors of cyclooxygenase-2 and are thereby useful in the treatment of cyclooxygenase-2 mediated diseases as enumerated above. The activities of the compounds against cyclooxygenase may be seen in the representative results shown below. In the assay, inhibition is determined by measuring the amount of prostaglandin $E_2$ ($PGE_2$) synthesized in the presence of arachidonic acid, cyclooxygenase-1 or cyclooxygenase-2 and a putative inhibitor. The $IC_{50}$ values represent the concentration of putative inhibitor required to return $PGE_2$ synthesis to 50% of that obtained as compared to the uninhibited control.

The results for inhibition of $PGE_2$ production may be seen in Table III.

| | | | $IC_{50}$ (µM) Whole cell | |
|---|---|---|---|---|
| A | B | C | COX-1 | COX-2 |
| Cl | Cl | Cl | >100 | 1.0 |
| Cl | Cl | H | >100 | 10.0 |

The invention is illustrated by the following non-limiting examples in which, unless stated otherwise:
  (i) all operations were carded out at room or ambient temperature, that is, at a temperature in the range 18°–25° C.,
  (ii) evaporation of solvent was carded out using a rotary evaporator under reduced pressure (600–4000 pascals: 4.5–30 mm. Hg) with a bath temperature of up to 60° C.,
  (iii) the course of reactions was followed by thin layer chromatography (TLC) and reaction times are given for illustration only;
  (iv) melting points are uncorrected and 'd' indicates decomposition; the melting points given are those obtained for the materials prepared as described; polymorphism may result in isolation of materials with different melting points in some preparations;
  (v) the structure and purity of all final products were assured by at least one of the following techniques: TLC, mass spectrometry, nuclear magnetic resonance (NMR) spectrometry or microanalytical data;
  (vi) yields are given for illustration only;
  (vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multipict; br. broad; etc.: in addition "Ar" signifies an aromatic signal;
  (viii) chemical symbols have their usual meanings; the following abbreviations have also been used v (volume), w (weight), b.p. (boiling point), m.p. (melting point), L (liter(s)), mL (milliliters), g (gram(s)), mg (milligrams(s)), tool (moles), mmol (millimoles), eq (equivalent(s)).

EXAMPLE 1

1-(2,4,6-Trichlorobenzoyl)-5-methoxy-2-methyl-3-indolyl acetic acid

Step 1: 5-Methoxy-2-methyl-3-indolyl acetic acid 2-(tfirnethyl
  silyl)ethyl ester To a mixture of 5-methoxy-2-methyl-3-indolyl acetic acid (8.9 g, Aldrich) and 2-trimethylsilylethanol (7.0 mL) in dichloromethane (100 mL) at 0° C. was added DMAP (500 mg) followed by 1-(3-dimethylaminopropyl)-3-ethylcarbodiimide hydrochloride (8.56 g) portionwise. After stirring overnight at room temperature, the reaction mixture was diluted with $CH_2Cl_2$ and washed with water (x2) and dried. The organic layer was evaporated to dryness and the residue was crystallized from EtOAc/hexane to give 9.3 g of the titled compound. Further reprocessing of the mother liquor afforded a further 2.0 g of the material to give a total of 11.3 g.

$^1$H NMR (acetone-$d_6$) δ0.02 (9H, s), 0.98 (2H, m), 2.38 (3H, s), 3.62 (2H, s), 3.78 (3H, s), 4.13 (2H, m), 6.66 (1H, dd), 6.97 (1H, d), 7.15 (1H, d), 9.70 (1H, bs).

Step 2: 1-(2,4,6-Trichlorobenzoyl)-5-methoxy-2-methyl-3-indolyl acetic acid 2-(trimethylsilyl)ethyl ester To 5-methoxy-2-methyl-3-indolyl acetic acid 2-(trimethylsilyl)ethyl ester (2.00 g) in THF (20.0 mL) was added HMPA (2.0 mL). To the resulting mixture at −78° C. was added a 0.5M toluene solution of KHMDS (13.8 mL). After a period of 0.5 h, 2,4,6-trichlorobenzoyl chloride (1.03 mL) was added and the mixture was stirred 0.5 h at −78° C. then 0.5 h at 0° C. An aqueous solution of $NH_4Cl$ was then added and extracted with EtOAc. After purification by flash chromatography (10% EtOAc in hexane) the title compound was obtained (2.80 g) and used as such for the next step.

Step 3: 1 -(2,4,6-Trichlorobenzoyl)-5-methoxy-2-methyl-3-indolyl acetic acid

To 1-(2,4,6-trichlorobenzoyl)-5-methoxy-2-methyl-3-indolyl acetic acid 2-(trimethylsilyl)ethyl ester (2.80 g) in THF (25.0 mL) at 0° C. was added TBAF (14.7 mL). After a period of 5 h at room temperature, the reaction mixture was acidified by the addition of $NH_4Cl$ and HCl, extracted with EtOAc, dried over $Na_2SO_4$ and evaporated. The resulting solid was washed with 10%

EtOAc in hexane and recrystallized (EtOAc-hexane) to afford 1.73 g of the title compound, m.p. 193°–196° C.

The following Examples were prepared according to the above-described methods.

EXAMPLE 2

1-(2,6-dichlorobenzoyl)-5-methoxy-2-methyl-3-indolyl acetic acid $^1$H NMR (400 MHz) CD$_3$COCD$_3$ mixture of rotamers in the ratio of 1.81.

Major rotamer δ 1.86 (3H, s), 3.70 (2H, s), 3.88 (3H, s), 6.97 (1H, m), 7.14 (1H, m), 7.65 (3H, m), 8.47 (1H, d).

Major rotamer δ2.75 (3H, s), 3.77 (2H, s), 3-.79 (3H, s), 5.96 (1H, d), 6.56 (1H, d), 7.15 (1H, m), 7.65 (3H, m).

What is claimed is:

1. A compound of structural formula:

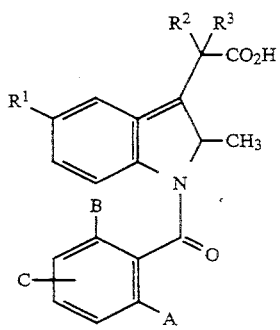

or a pharmaceutically acceptable salt thereof, wherein:
R$^1$ is —OCH$_3$, —N(CH$_3$)$_2$, —SCH$_3$, —OCF$_3$, halo or lower alkyl; R$^2$ and R$^3$ are independently H or lower alkyl or R$^2$ and R$^3$ may be joined to form a saturated hydrocarbon ring of 3 to 7 members;

A is halogen, lower alkoxy, lower alkylthio, lower alkylsulfinyl, lower alkylsulfonyl, CF$_3$, CN, N$_3$, NO$_2$, SCF$_3$ or OCF$_3$;

B is A; and

C is A.

2. The compound of claim 1 of structural formula:

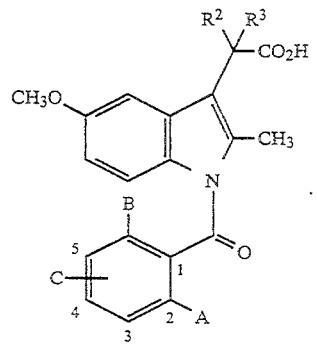

3. A compound of claim 2 selected from the group consisting of those depicted in the following table:

TABLE I

| A | B | C | R$^2$ | R$^3$ |
|---|---|---|---|---|
| Cl | Cl | 4-Cl | H | H |
| Cl | Cl | 4-Cl | CH$_3$ | H |
| Br | Cl | 4-Cl | H | H |
| CF$_3$ | Cl | 4-Cl | CH$_3$ | CH$_3$ |
| Cl | Cl | 4-S(O)$_2$CH$_3$ | H | H |
| Cl | Cl | 4-SCH$_3$ | H | H |
| Cl | Cl | 4-S(O)CH$_3$ | H | H |
| SCH$_3$ | Cl | 4-Cl | H | H |
| SCF$_3$ | Cl | 4-Cl | H | H |
| S(O)$_2$CH$_3$ | Cl | 4-Br | H | H. |

4. A compound which is

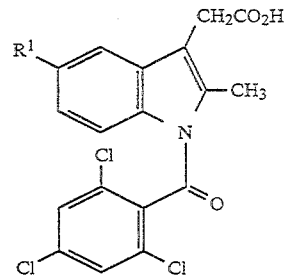

wherein R$^1$ is —F, —Cl, —CH(CH$_3$)$_2$, —N(CH$_3$)$_2$, —SCH$_3$ or —OCF$_3$.

5. An anti-inflammatory pharmaceutical formulation comprising a pharmaceutically acceptable carrier and an anti-inflammatory effective amount of compound of claim 1.

6. A method of treating inflammation in a patient in need of such treatment which comprises the administration of an effective amount of the compound of claim 1.

7. An anti-inflammatory pharmaceutical formulation comprising a pharmaceutically acceptable carrier and an anti-inflammatory effective amount of compound of claim 4.

8. A method of treating inflammation in a patient in need of such treatment which comprises the administration of an effective amount of the compound of claim 4.

* * * * *